United States Patent
Watanabe et al.

(10) Patent No.: US 10,029,981 B2
(45) Date of Patent: Jul. 24, 2018

(54) PROCESS FOR PRODUCING PERFLUOROPOLYOXYALKYLENE PEROXIDE COMPOUND

(71) Applicant: DAIKIN INDUSTRIES, LTD., Osaka-shi, Osaka (JP)

(72) Inventors: Keiichirou Watanabe, Osaka (JP); Hideki Nakaya, Osaka (JP); Motohisa Shino, Osaka (JP); Tatsuya Takakuwa, Osaka (JP); Kazunori Morimoto, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/373,131

(22) Filed: Dec. 8, 2016

(65) Prior Publication Data
US 2017/0166522 A1 Jun. 15, 2017

(30) Foreign Application Priority Data
Dec. 10, 2015 (JP) .................................. 2015-241513

(51) Int. Cl.
C07C 407/00 (2006.01)
(52) U.S. Cl.
CPC ................. *C07C 407/00* (2013.01)

(58) Field of Classification Search
CPC ................................................... C07C 407/00
See application file for complete search history.

(56) References Cited

U.S. PATENT DOCUMENTS

| | | | |
|---|---|---|---|
| 3,458,535 A | 7/1969 | Gozzo et al. | |
| 5,149,842 A | 9/1992 | Sianesi et al. | |
| 5,354,922 A | 10/1994 | Marchionni et al. | |
| 7,214,833 B2 * | 5/2007 | Marchionni | C08G 65/3236 568/615 |

FOREIGN PATENT DOCUMENTS

| | | | |
|---|---|---|---|
| CA | 785315 | A | 5/1968 |
| EP | 1702940 | A1 | 9/2006 |
| JP | 4-505171 | A | 9/1992 |
| JP | 6-128373 | A | 5/1994 |

OTHER PUBLICATIONS

Communication dated Mar. 24, 2017 issued by the European Patent Office in counterpart European Application No. 16203165.2.

* cited by examiner

*Primary Examiner* — Sikarl A Witherspoon
(74) *Attorney, Agent, or Firm* — Sughrue Mion, PLLC

(57) ABSTRACT

The present invention provides a process for producing a perfluoropolyoxyalkylene peroxide compound comprising a step of reacting a perfluoroalkene with oxygen, wherein the reaction of the perfluoroalkene with oxygen is performed in a microreactor.

15 Claims, No Drawings

PROCESS FOR PRODUCING PERFLUOROPOLYOXYALKYLENE PEROXIDE COMPOUND

TECHNICAL FIELD

The present invention relates to a process for producing a perfluoropolyoxyalkylene peroxide compound.

BACKGROUND ART

A perfluoropolyether compound is widely used as a lubricant, an intermediate of various polymers, or the like and its application has been further expanded. The perfluoropolyoxyalkylene peroxide compound is known as a raw material of the perfluoropolyether compound. The perfluoropolyether compound can be obtained by the degradation or the reduction of the perfluoropolyoxyalkylene peroxide compound.

As a process for producing the perfluoropolyoxyalkylene peroxide compound, for example, a method in which tetrafluoroethylene is reacted with oxygen is known. Representatively, the reaction is performed by reacting tetrafluoroethylene with oxygen under an ultraviolet irradiation (Patent Document 1). Alternatively, a method is known wherein the reaction of tetrafluoroethylene with oxygen is started by adding a fluorine source, for example, $F_2$, a FO-alkyl or the like without the ultraviolet irradiation (Patent Document 2). These reactions have been performed as a batch reaction by using a reactor having a general size (in Patent Documents 1 and 2, a grass reactor of 500 mL).

PRIOR ART DOCUMENT

Patent Document

Patent Document 1: Japanese Laid-Open Patent Publication No. 6-128373
Patent Document 2: Japanese Laid-Open Patent Publication No. 4-505171

SUMMARY OF THE INVENTION

Problem to be Solved by the Invention

As the application of the perfluoropolyether compound is expanded, a demand to provide perfluoropolyether compounds having various variations of a molecular weight or a backbone structure is increased. That is, also as to the perfluoropolyoxyalkylene peroxide compound which is a raw material of the perfluoropolyether compound, a method is required which is able to produce perfluoropolyoxyalkylene peroxide compounds having various variations of a molecular weight or a backbone structure. However, it is difficult to obtain the perfluoropolyoxyalkylene peroxide having various variations of a molecular weight or a backbone structure by using the methods of Patent Documents 1 and 2.

Furthermore, in the batch reaction described above, a hydrochlorofluorocarbon (HCFC) solvent or a chlorofluorocarbon (CFC) solvent is used as a solvent in order to prevent the precipitation of a polymer produced in the reaction. However, the HCFC solvent or the CFC solvent is an ozone-depleting substance and a greenhouse effect gas, therefore, these use is not preferable.

An object of the present invention is to provide a process for producing which is able to efficiently obtain the perfluoropolyoxyalkylene peroxide compound having a specific physical property or a process for producing which is able to be performed without using the HCFC solvent or the CFC solvent.

Means to Solve the Problem

As a result of intensively studying, the inventors of the present invention have found that by performing the reaction of the perfluoroalkene with oxygen in the microreactor, it becomes possible to successfully perform the reaction without using the HCFC solvent or the CFC solvent and obtain the perfluoropolyoxyalkylene peroxide compound having a specific physical property, and have reached the present invention.

According to an aspect of the present invention, there is provided a process for producing a perfluoropolyoxyalkylene peroxide compound comprising a step of reacting a perfluoroalkene with oxygen, wherein the reaction of the perfluoroalkene with oxygen is performed in a microreactor.

One embodiment is the process for producing described above further comprising a step of introducing a fluorine source into a reaction mixture containing the perfluoroalkene and oxygen.

Another embodiment is the process for producing described above further comprising a step of light-irradiating a reaction mixture of the perfluoroalkene and oxygen.

Another embodiment is the process for producing described above further comprising a step of introducing a fluorine source into a reaction mixture of the perfluoroalkene and oxygen and light-irradiating the reaction mixture.

Effect of the Invention

According to the present invention, by performing the reaction of the perfluoroalkene with oxygen in the microreactor, the perfluoropolyoxyalkylene peroxide compound having a specific physical property can be obtained without using the HCFC solvent or the CFC solvent.

EMBODIMENTS TO CARRY OUT THE INVENTION

Hereinafter, the process for producing of the present invention will be described.

The term "perfluoroalkene" as used herein represents a compound wherein all of hydrogen atoms of an alkene are substituted with a fluorine atom.

The term "alkene" described above represents a straight or branched unsaturated hydrocarbon having one double bond.

With respect to the perfluoroalkene, the number of carbon in the alkene chain is preferably 2 to 12, preferably 2 to 8, more preferably 2 to 6, particularly preferably 2.

The perfluoroalkene used in the present invention is preferably straight. The perfluoroalkene used in the present invention is preferably a compound having the double bond at the molecular terminal of the following formula:

$R^1$—CF=CF$_2$ wherein $R^1$ is a fluorine atom or a perfluoroalkyl group having 1 to 11 carbon atoms.

$R^1$ may be preferably a fluorine atom or a perfluoroalkyl group having 1 to 5 carbon atoms, for example trifluoromethyl, pentafluoroethyl, heptafluoro-n-propyl, nonafluoro-n-butyl, undecafluoro-n-pentyl, more preferably a fluorine atom.

The perfluoroalkene as used herein is preferably tetrafluoroethylene or hexafluoropropene, more preferably tetrafluoroethylene.

The perfluoroalkene may further have a substituent. Examples of the substituent include, but are not particularly limited to, for example one or more groups selected from a halogen atom (for example, a fluorine atom, a chlorine atom, a bromine atom, or the like); and a $C_{1-6}$ alkyl group, a $C_{2-6}$ alkenyl group, a $C_{2-6}$ alkynyl group, a $C_{3-10}$ cycloalkyl group, a $C_{3-10}$ unsaturated cycloalkyl group, a 5-10 membered heterocyclyl group, a 5-10 membered unsaturated heterocyclyl group, a $C_{6-10}$ aryl group, and a 5-10 membered heteroaryl group, which may be substituted by one or more halogen atoms.

In a preferable embodiment, the perfluoroalkene described above does not have the above substituent.

The perfluoropolyoxyalkylene peroxide compound produced by the process for producing of the present invention is a compound having a peroxide structure (—O—O—) and a perfluoropolyether structure ($—(C_nF_{2n}O)_m—$) in its molecular. In $—(C_nF_{2n}O)_m—$ described above, n is an integer independently selected in the respective units in parentheses with the subscript m, for example an integer of to 12, preferably an integer of 1 to 4, and m is an arbitrary integer, preferably an integer of 2 to 2,000, for example, an integer of 20 to 2,000.

In a preferably embodiment, the perfluoropolyoxyalkylene peroxide compound is a compound of the following formula (I).

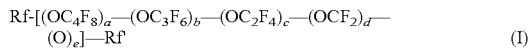

Rf-[(OC$_4$F$_8$)$_a$—(OC$_3$F$_6$)$_b$—(OC$_2$F$_4$)$_c$—(OCF$_2$)$_d$— (O)$_e$]—Rf'    (I)

In the above formula, Rf and Rf' are each independently —CF$_3$, —CF$_2$CF$_3$, —COF or —CF$_2$COF.

In the above formula, a and b may be each independently an integer of 0 to 100, for example an integer of 1 to 100, preferably an integer of 0 to 50, more preferably an integer of 0 to 30. In the above formula, c and d may be each independently an integer of 0 to 1,000, for example an integer of 2 to 1,000, preferably an integer of 0 to 800, more preferably an integer of 2 to 600, for example, an integer of 10 to 600. The sum of a, b, c and d may be an integer 2 to 2,000, preferably an integer of 2 to 1,500, more preferably an integer of 2 to 1,000, for example an integer of 100 to 800 or an integer of 250 to 800. In the above formula, e may be an integer of 0 to 250, for example an integer of 1 or more or 5 or more and 250 or less, preferably an integer of 0 to 150, more preferably an integer of 0 to 100, for example 50 or less, 40 or less or 35 or less.

The occurrence order of the respective repeating units in parentheses with the subscript a, b, c, d or e is not limited in the formula. Among these repeating units, the —(OC$_4$F$_8$)— group may be any of —(OCF$_2$CF$_2$CF$_2$CF$_2$)—, —(OCF(CF$_3$) CF$_2$CF$_2$)—, —(OCF$_2$CF(CF$_3$)CF$_2$)—, —(OCF$_2$CF$_2$CF(CF$_3$))—, —(OC(CF$_3$)$_2$CF$_2$)—, —(OCF$_2$C(CF$_3$)$_2$)—, —(OCF(CF$_3$)CF(CF$_3$))—, —(OCF(C$_2$F$_5$)CF$_2$)— and —(OCF$_2$CF(C$_2$F$_5$)), preferably —(OCF$_2$CF$_2$CF$_2$CF$_2$)—. The —(OC$_3$F$_6$)— group may be any of —(OCF$_2$CF$_2$CF$_2$)—, —(OCF(CF$_3$) CF$_2$)— and —(OCF$_2$CF(CF$_3$))—, preferably —(OCF$_2$CF$_2$CF$_2$)—. The —(OC$_2$F$_4$)— group may be any of —(OCF$_2$CF$_2$)— and —(OCF(CF$_3$))—, preferably —(OCF$_2$CF$_2$)—.

In one embodiment, the perfluoropolyoxyalkylene peroxide compound may be a compound of the following formula.

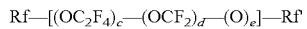

Rf—[(OC$_2$F$_4$)$_c$—(OCF$_2$)$_d$—(O)$_e$]—Rf'

In one embodiment, a number average molecular weight of the perfluoropolyoxyalkylene peroxide compound is, for example, 5,000 or more, preferably 10,000 or more, more preferably 15,000 or more, further preferably 20,000 or more, further more preferably 25,000 or more. An upper limit of the number average molecular weight of the perfluoropolyoxyalkylene peroxide compound is not particularly limited. For example, the number average molecular weight of the perfluoropolyoxyalkylene peroxide compound may be 150,000 or less, 100,000 or less or 50,000 or less.

In the present invention, the number average molecular weight of the perfluoropolyoxyalkylene peroxide compound is measured by a GPC (Gel permeation chromatography) analysis unless indicated otherwise.

In one embodiment, a ratio of c to d (hereinafter, referred to as a "c/d ratio" or an "EM ratio") is 0.1 or more and 5.0 or less, preferably 0.3 or more and 4.0 or less, more preferably 0.5 or more and 3.0 or less, preferably 2.0 or less or 1.2 or less, for example 0.7 or more and 2.0 or less or 0.8 or more and 1.2 or less.

In the present invention, the EM ratio is measured by a $^{19}$F-NMR analysis.

In one embodiment, a PO value of the perfluoropolyoxyalkylene peroxide compound is 8.6 or less, preferably 7.0 or less. A lower limit of the PO value is, preferably 1.0 or more, more preferably 3.0 or more. The PO value represents a mass of a reactive oxygen (one oxygen of oxygens forming —O—O—) contained in 100 g of a compound.

In the present invention, the PO value is measured by a $^{19}$F-NMR analysis.

In a preferable embodiment, the perfluoropolyoxyalkylene peroxide compound meets at least two, preferably all of following requirements (a) to (c):

(a) the number average molecular weight is 5,000 or more, preferably 15,000 or more, (b) the EM ratio is 0.1 to 5.0, preferably 0.7 to 2.0, and (c) the PO value is 8.6 or less, preferably 7.0 or less.

When the above requirements (a) and/or (c) are met, a molecular weight of the perfluoropolyether compound obtained by the degradation or the reduction of the perfluoropolyoxyalkylene peroxide compound can become higher. When the above requirement (b) is met, the perfluoropolyether compound having the similar EM ratio to that of the perfluoropolyoxyalkylene peroxide compound can be obtained. By using the perfluoropolyether compound having higher number average molecular weight and the EM ratio of 0.1 to 5.0, preferably 0.5 to 3.0, more preferably 0.7 to 2.0, for example, a perfluoropolyether group-containing silane compound providing excellent effect as a water and oil repellent can be obtained.

In the process for producing of the present invention, the reaction of the perfluoroalkene with oxygen is performed in a microreactor.

The microreactor as used herein represents a reactor having a channel width which does not completely separate reaction liquids and does not generate an interface between the liquids.

The channel width of the microreactor may be preferably 10 mm or less, more preferably 1 μm or more and 8.0 mm or less, further preferably 10 μm or more and 6.0 mm or less, further more preferably 100 μm or more and 5.0 mm or less, for example 4.9 mm or less, 4.8 mm or less, 4.5 mm or less, 4.0 mm or less or 3.0 mm or less. By making the channel width larger, throughput can be increased. By making the channel width smaller, the molecular contact (in other words, microscopic mixing) of the perfluoroalkene with oxygen can be sufficiently attained, as a result of which the reaction is allowed to rapidly proceed and the reaction time (or residence time) can be shortened. In addition, effective heat removal and strict temperature control become possible. Furthermore, by making the channel width smaller, rapid reaction or degradation of reactants (for example, tetrafluoroethylene) in the reactor can be suppressed, and even if the rapid reaction or degradation occurs, the effects can be minimized. It is noted that the channel width represents a smallest distance between opposing walls of the channel. When light irradiation is performed, since reaction effectivity can be increased by making the channel width in a direction of the light irradiation larger, the channel width in a direction of the light irradiation is not limited.

The perfluoroalkene introduced into the microreactor may be in a state of gas or liquid, and the state is appropriately selected depending on the perfluoroalkene used and reaction conditions such as temperature, pressure, or the like. In one embodiment, the perfluoroalkene introduced into the microreactor is in a state of gas. In another embodiment, the perfluoroalkene introduced into the microreactor is dissolved in a following solvent.

A flow rate of the perfluoroalkene may be preferably 0.01 to 100 mL/min, more preferably 0.1 to 10 mL/min calculated in term of a state at ambient temperature (25° C.) and under ambient pressure (1 atom).

An oxygen source introduced into the microreactor is preferably an oxygen gas ($O_2$).

The oxygen gas to be supplied may be supplied to the reaction system as only an oxygen gas, as a mixture of oxygen and other inert gasses such as a nitrogen gas, or as air.

A flow rate of the oxygen may be preferably 0.01 to 200 mL/min, more preferably 1.0 to 20 mL/min in term of a state at ambient temperature (25° C.) and under ambient pressure (1 atom).

A volume ratio of the oxygen to the perfluoroalkene to be introduced into the microreactor (an oxygen/perfluoroalkene ratio) may be, but not particularly limited to, for example, 0.1 to 20, preferably 0.1 to 10, more preferably 0.4 to 10, further preferably 1.0 to 8.0.

The reaction of the perfluoroalkene with the oxygen is preferably performed in a solvent. By performing the reaction in the solvent, a polymerization between the perfluoroalkenes and a precipitation of an obtained polymer can be suppressed.

The solvent is not limited as long as the perfluoroalkene can be dissolved in the solvent. Examples of the solvent include, for example, a perfluorocarbon (PFC) solvent such as perfluorohexane. A preferable solvent is perfluorohexane. In the process for producing of the present invention, since the reaction is performed in the microreactor, the reaction can be performed without using the HCFC solvent (for example, chlorodifluoromethane (R22)) or the CFC solvent.

The solvent and the perfluoroalkene may be mixed and then, introduced into the microreactor in a state of a mixture or a solution. Alternatively the solvent and the perfluoroalkene may be introduced into the microreactor respectively and mixed or dissolved in the microreactor.

A flow rate of the solvent is preferably 0.01 to 100 mL/min, more preferably 0.1 to 10 mL/min.

A temperature in the microreactor is not limited as long as the reaction of the perfluoroalkene with oxygen can proceed, and may be, for example, −100 to 30° C., preferably −80 to 0° C.

A pressure in the microreactor is not limited as long as the reaction of the perfluoroalkene with oxygen can proceed, and may be, for example, 0.1 to 1.0 MPa, preferably 0.1 to 0.5 MPa.

A reaction time (or a residence time) in the microreactor may be, for example, 0.1 second to 1 hour, preferably 0.1 second to 30 minutes, for example, 0.1 second to 30 minutes.

The reaction of the perfluoroalkene with oxygen may be started or facilitated by performing any one of following three operations (i) to (iii):
(i) introducing the fluorine source into the reaction mixture;
(ii) light-irradiating the reaction mixture; or
(iii) introducing the fluorine source into and light-irradiating the reaction mixture.

By performing the reaction as described above, with the respect to the obtained perfluoropolyoxyalkylene peroxide compound, it becomes possible to make the number average molecular weight higher, make the EM ratio lower, or make the PO value lower. For example, the perfluoropolyoxyalkylene peroxide compound having 5,000 or more of the number average molecular weight, 0.1 to 5.0 of the EM ratio, and/or 8.6 or less of the PO value.

Hereinafter, the operations (i) to (iii) described above will be described in more detail.

Operation (i)

The introducing of the fluorine source may be performed by adding the fluorine source to the reaction mixture of the perfluoroalkene and oxygen, or by mixing one of the perfluoroalkene and oxygen with the fluorine source before the introducing. In one embodiment, the introducing of the fluorine source is performed by adding the fluorine source to the reaction mixture.

The present invention is not bounded by any theory, although it is considered that by introducing the fluorine source, the perfluoroalkene is reacted with fluorine, and a double bond of the perfluoroalkene is cleaved to generate a perfluoroalkyl radical. It is considered that this radical is reacted with oxygen, as a result of which the reaction proceeds. Since this starting reaction proceeds at a relatively rapid rate, the introducing of the fluorine source increases the reaction rate of the perfluoroalkene with oxygen. In addition, it becomes possible to make the PO value of the perfluoropolyoxyalkylene peroxide compound lower.

Examples of the fluorine source described above include $F_2$ or $R^{11}$—OF (wherein $R^{11}$ is a perfluoroalkyl group having 1 to 6 carbons.). The fluorine source is preferably $F_2$ gas.

The fluorine source may be introduced into the microreactor directly, or may be introduced in a state of a mixture of the fluorine source with other materials, for example, nitrogen gas. When the fluorine source is mixed with the other materials, a concentration of the fluorine source may be, but are not particularly limited to, for example, 1 to 50% by volume, preferably 10 to 30% by volume.

An amount used of fluorine (an amount of fluorine present in the reaction system) with respect to the perfluoroalkene may be preferably 0.001 to 1 mole, more preferably 0.005 to 0.1 mole, for example 0.01 to 0.1 mole with respect to 1 mole of the perfluoroalkene.

A flow rate of the fluorine source may be preferably 0.001 to 5 mL/min, more preferably 0.005 to 0.5 mL/min, further preferably 0.005 to 0.1 mL/min, for example 0.01 to 0.05 mL/min calculated in term of an alone state of the fluorine source at ambient temperature (25° C.) and under ambient pressure (1 atom).

When fluorine is used, the reaction time (or the residence time) in the microreactor may be, for example, 0.1 second to 10 minutes, preferably 0.5 seconds to 1 minute, for example, 1 second to 10 seconds.

Operation (ii)

The light irradiation is performed such that a subject to be irradiated is a mixture contained in the microreactor. Therefore, when the light irradiation is performed, a material constituting the microreactor may be a material which a light having a prescribed wavelength penetrates, for example, a glass.

The present invention is not bound by any theory, although it is considered that by performing the light-irradiation, the perfluoroalkene is reacted with oxygen to generate a biradical, as a result of which the reaction is started. In addition, by performing the light-irradiation, a —O—O— bonding in a molecular chain of a molecular whose reaction is stopped is cleaved to generate a radical again, and an extension reaction proceeds. As a result, the molecular having a higher molecular weight can be obtained.

The light to be used is a light having preferably a wavelength of 200 nm to 350 nm, more preferably a wavelength of 220 nm to 280 nm. By the irradiation is performed by using the light having such wavelength, the reaction becomes effective.

Examples of the light source having the wavelength described above include, for example, a mercury lamp, a xenon lamp, a LED lamp, an excimer lamp, a lamp of an electron beam or the like. The mercury lamp may be a low pressure mercury lamp, a medium mercury lamp, or a high pressure mercury lamp.

A density of the light irradiation may be preferably 0.01 W/m$^2$ to 500 W/m$^2$, more preferably 0.01 W/m$^2$ to 300 W/m$^2$ on the surface of the reaction site. By making the density of irradiation of the light having the wavelength of 220 nm to 280 nm higher, the reaction rate can be controlled. That is, the EM ratio and the PO value can be controlled.

In one embodiment, the wavelength of the light to be used is 220 nm to 280 nm, the density of the light irradiation is 80 W/m$^2$ to 300 W/m$^2$, the reaction temperature is −100 to 25° C., and the residence time is 0.1 second to 60 minutes.

In one embodiment, the reaction temperature can be changed depending on the location. For example, the temperature is higher in an early phase of the reaction, and then the temperature may be lowered. For example, the reaction temperature can be relatively higher (for example, −30 to 30° C., preferably, −30 to 10° C.) in an early phase of the reaction (for example, for 1 to 5 minutes after starting the reaction), and then the temperature can be relatively lower (for example, −100 to 0° C., preferably −80° C. to −20° C.). As such described, by setting the temperature in the early phase of the reaction to higher, and then lowering the temperature, the effectiveness of the reaction can be increased. On the other hand, the temperature may be lowered in the early phase of the reaction, and then the temperature may be raised.

When the light irradiation is performed, the reaction time (or the residence time) in the microreactor may be, for example, 10 seconds to 1 hour, preferably 30 seconds to 30 minutes, for example 1 to 30 minutes.

Operation (iii)

The addition of the fluorine source is performed similarly to Operation (i) described above, and the light irradiation is performed similarly to Operation (ii) described above. That is, Operation (iii) is a combination of the Operation (i) and Operation (ii). By combining Operation (i) and Operation (ii), the reaction rate of the perfluoroalkene with oxygen is increased, and a perfluoropolyoxyalkylene peroxide compound having a relatively lower PO value and a relatively higher molecular weight can be obtained.

As described above, the perfluoropolyoxyalkylene peroxide compound is produced. The process for producing the perfluoropolyoxyalkylene peroxide compound can be performed in a form of a continuous type.

EXAMPLES

Examples 1 and 2

As the microreactor, a reactor was used wherein a channel of stainless which has a channel width of 2 mm, a channel depth of 5 mm, a length of 652.8 mm, was a ditched groove which was folded per 41 mm, and was covered and sealed with a silica glass. An inlet port of the microreactor was connected to a tetrafluoroethylene (TFE) tank, an oxygen (O$_2$) tank, and a perfluorohexane (PFH) tank via a precooling section, respectively.

From each raw material tank, TFE (1 mL/min), oxygen (6 mL/min), and PFH (0.24 mL/min) were supplied to a fine tube and were cooled to −45° C. (Example 1) or −60° C. (Example 2) in the precooling section, and were supplied to the microreactor. The microreactor was irradiated with a light having the wavelength of 220 nm to 280 nm at the light irradiation density of 200 W/m$^2$ using a high pressure mercury lamp as a light source.

Evaluation

The obtained products were evaluated as follows, and a yield, a number average molecular weight, an EM ratio, a PO value were calculated. The results are shown in the following table.

Yield

From the result of a $^{19}$F-NMR analysis, a fluorine amount incorporated into the polymer in the product and a fluorine amount in TFE were determined, and the yield was calculated according to the following equation:

Yield=(Fluorine amount incorporated into the peroxide polymer in the production)/(Fluorine amount in TFE)×100(%)

Number Average Molecular Weight From the result of the $^{19}$F-NMR analysis, a ratio of the number of units of CF$_2$CF$_2$OO, CF$_2$CF$_2$O, CF$_2$OO and CF$_2$O, and terminal CF$_3$ in a main chain of the peroxide polymer in the product was determined, and the number average molecular weight (Mn) was calculated according to the following equations:

The number of each unit in the main chain of the polymer per one molecular of the polymer=Ratio of each unit/((Ratio of terminal CF$_3$)/2)

Number average molecular weight (Mn)=

{Molecular weight of the main chain}+{(Molecular weight of the terminal CF$_3$)×2}

={(The number of unit CF$_2$CF$_2$OO×132)+(The number of unit CF$_2$CF$_2$O×116)+(The number of unit CF$_2$OO×82)+(The number of unit CF$_2$O×66)}+ {2×69}

EM Ratio

From the result of the $^{19}$F-NMR analysis, the number of unit CF$_2$CF$_2$ and the number of unit CF$_2$ in the product were determined, and the EM ratio was calculated according to the following equation:

EM ratio=(The number of unit CF$_2$CF$_2$)/(The number of unit CF$_2$)

PO Value

From the result of the $^{19}$F-NMR analysis, the number of unit CF$_2$CF$_2$OO and the number of unit CF$_2$OO in the product were determined, a molecular weight of a reactive oxygen and a molecular weight of the polymer in the product were calculated, and the PO ratio was calculated according to the following equations:

Molecular weight of the reactive oxygen=(The number of unit $CF_2CF_2OO \times 16$)+(The number of unit $CF_2OO \times 16$)

Molecular weight of polymer as a whole=(The number of unit $CF_2CF_2OO \times 132$)+(The number of unit $CF_2CF_2O \times 116$)+(The number of unit $CF_2OO \times 82$)+(The number of unit $CF_2O \times 66$)+(The number of unit $CF_3 \times 69$)

PO value=(Molecular weight of the reactive oxygen)/(Molecular weight of polymer as a whole)

TABLE 1

| | Experiment condition | | | |
|---|---|---|---|---|
| | TFE (mL/min) | $O_2$ (mL/min) | PFH (mL/min) | Temp. (° C.) |
| Example 1 | 1 | 6 | 0.24 | −45 |
| Example 2 | 1 | 6 | 0.24 | −60 |

| | Result | | | |
|---|---|---|---|---|
| | PO value | EM ratio | Yield (%) | Mn |
| Example 1 | 8.6 | 1.00 | 22 | 19,936 |
| Example 2 | 7.5 | 1.51 | 37 | 18,512 |

Examples 3 and 4

Reactions were performed similarly to Examples 1 and 2, respectively, except that a fluorine (15% of $F_2$ in $N_2$) tank was further connected to the microreactor. The evaluation was performed similarly to Examples 0.1 and 2 to determine the yield, the EM ratio, and the PO value. The number average molecular weight was measured by using a GPC (gel permeation chromatography) analysis. The results are shown in the following table.

TABLE 2

| | Experiment condition | | | | |
|---|---|---|---|---|---|
| | TFE (mL/min) | $O_2$ (mL/min) | $F_2$ (mL/min) | PFH (mL/min) | Temp. (° C.) |
| Example 3 | 1 | 6 | 0.11 | 0.24 | −45 |
| Example 4 | 1 | 6 | 0.11 | 0.24 | −60 |

| | Result | | | |
|---|---|---|---|---|
| | PO value | EM ratio | Yield (%) | Mn |
| Example 3 | 6.7 | 0.84 | 27 | 6,068 |
| Example 4 | 7.3 | 1.28 | 34 | 7,513 |

Examples 5 and 6

Reactions were performed similarly to Examples 3 and 4, respectively, except that the light irradiation was not performed. The evaluation was performed similarly to Examples 1 and 2 to determine the yield, the number average molecular weight, the EM ratio, and the PO value. The results are shown in the following table.

TABLE 3

| | Experiment condition | | | | |
|---|---|---|---|---|---|
| | TFE (mL/min) | $O_2$ (mL/min) | $F_2$ (mL/min) | PFH (mL/min) | Temp. (° C.) |
| Example 5 | 1 | 6 | 0.11 | 0.24 | −45 |
| Example 6 | 1 | 6 | 0.11 | 0.24 | −60 |

| | Result | | | |
|---|---|---|---|---|
| | PO value | EM ratio | Yield (%) | Mn |
| Example 5 | 4.3 | 0.44 | 6.4 | 1,495 |
| Example 6 | 6.9 | 0.85 | 5.1 | 2,783 |

As seen from the above results, it was confirmed that by performing the reaction of the perfluoroalkene with oxygen in the microreactor, even if the perfluorocarbon solvent was used, the reaction successfully proceeded. It was confirmed that by adding fluorine to the reaction mixture, the PO value and the EM ratio of the perfluoropolyoxyalkylene peroxide compound could be lowered. It was confirmed that by irradiating the reaction mixture with the light, the perfluoropolyoxyalkylene peroxide compound having a higher molecular weight could be obtained. It is confirmed that by adding fluorine to the reaction mixture and irradiating the reaction mixture with the light, the perfluoropolyoxyalkylene peroxide compound having a relatively higher molecular weight, a relatively lower PO value and EM ratio could be obtained.

The present invention includes following embodiments:

Embodiment 1

A process for producing a perfluoropolyoxyalkylene peroxide compound comprising a step of reacting a perfluoroalkene with oxygen, wherein the reaction of the perfluoroalkene with oxygen is performed in a microreactor.

Embodiment 2

The process for producing according to Embodiment 1, further comprising a step of introducing a fluorine source into a reaction mixture containing the perfluoroalkene and oxygen.

Embodiment 3

The process for producing according to Embodiment 2, wherein the fluorine source is $F_2$.

Embodiment 4

The process for producing according to Embodiment 1, further comprising a step of light irradiating a reaction mixture of the perfluoroalkene and oxygen.

Embodiment 5

The process for producing according to Embodiment 4, wherein the light irradiation is performed by irradiating the reaction mixture with a light having a wavelength of 200 nm to 350 nm.

Embodiment 6

The process for producing according to Embodiment 1, further comprising a step of introducing a fluorine source into a reaction mixture of the perfluoroalkene and oxygen and light irradiating the reaction mixture.

Embodiment 7

The process for producing according to Embodiment 6, wherein the fluorine source is $F_2$, and the light irradiation is performed by irradiating the reaction mixture with a light having a wavelength of 200 nm to 350 nm.

Embodiment 8

The process for producing according to any one of Embodiments 1-7, wherein the perfluoroalkene is tetrafluoroethylene.

Embodiment 9

The process for producing according to any one of Embodiments 1-8, wherein the perfluoropolyoxyalkylene peroxide compound is a compound of the formula (I):

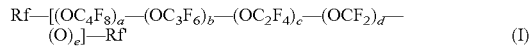
(I)

wherein:
Rf and Rf' are each independently —$CF_3$, —$CF_2CF_3$, —COF or —$CF_2COF$,
a and b are each independently an integer of 0 to 100,
c and d are each independently an integer of 2 to 1,000,
the sum of a, b, c and d is a integer of 2 to 2,000,
e is an integer of 0 to 250, and
the occurrence order of the respective repeating units in parentheses with the subscript a, b, c, d or e is not limited in the formula.

Embodiment 10

The process for producing according to Embodiment 9, wherein a c/d ratio of the perfluoropolyoxyalkylene peroxide compound is 5.0 or less.

Embodiment 11

The process for producing according to any one of Embodiments 1-10, wherein a PO value of the perfluoropolyoxyalkylene peroxide compound is 8.6 or less.

Embodiment 12

The process for producing according to any one of Embodiments 1-11, wherein a number average molecular weight of the perfluoropolyoxyalkylene peroxide compound is 5,000 or more.

Embodiment 13

The process for producing according to any one of Embodiments 1-12, wherein a channel width of the microreactor is 10 mm or less.

Embodiment 14

The process for producing according to any one of Embodiments 1-13, wherein a channel width of the microreactor is 5.0 mm or less.

INDUSTRIAL APPLICABILITY

According to the present invention, the perfluoropolyoxyalkylene peroxide compound can be suitably produced.

The invention claimed is:

1. A process for producing a perfluoropolyoxyalkylene peroxide compound comprising a step of reacting a perfluoroalkene with oxygen, wherein the reaction of the perfluoroalkene with oxygen is performed at −100° C. to 30° C. in a microreactor.

2. The process for producing according to claim 1, further comprising a step of introducing a fluorine source into a reaction mixture containing the perfluoroalkene and oxygen.

3. The process for producing according to claim 2, wherein the fluorine source is $F_2$.

4. The process for producing according to claim 1, further comprising a step of light irradiating a reaction mixture of the perfluoroalkene and oxygen.

5. The process for producing according to claim 4, wherein the light irradiation is performed by irradiating the reaction mixture with a light having a wavelength of 200 nm to 350 nm.

6. The process for producing according to claim 1, further comprising a step of introducing a fluorine source into a reaction mixture of the perfluoroalkene and oxygen and light irradiating the reaction mixture.

7. The process for producing according to claim 6, wherein the fluorine source is $F_2$, and the light irradiation is performed by irradiating the reaction mixture with a light having a wavelength of 200 nm to 350 nm.

8. The process for producing according to claim 1, wherein the perfluoroalkene is tetrafluoroethylene.

9. The process for producing according to claim 1, wherein the perfluoropolyoxyalkylene peroxide compound is a compound of the formula (I):

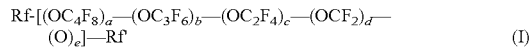
(I)

wherein:
Rf and Rf' are each independently —$CF_3$, —$CF_2CF_3$, —COF or —$CF_2COF$,
a and b are each independently an integer of 0 to 100,
c and d are each independently an integer of 2 to 1,000,
the sum of a, b, c and d is a integer of 2 to 2,000,
e is an integer of 0 to 250, and
the occurrence order of the respective repeating units in parentheses with the subscript a, b, c, d or e is not limited in the formula.

10. The process for producing according to claim 1, wherein the perfluoroalkene is tetrafluoroethylene, and
the perfluoropolyoxyalkylene peroxide compound is a compound of the formula (I):

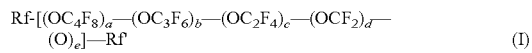
(I)

wherein:
Rf and Rf' are each independently —$CF_3$, —$CF_2CF_3$, —COF or —$CF_2COF$,
a and b are each independently an integer of 0 to 100,
c and d are each independently an integer of 2 to 1,000,
the sum of a, b, c and d is a integer of 2 to 2,000,
e is an integer of 0 to 250, and
the occurrence order of the respective repeating units in parentheses with the subscript a, b, c, d or e is not limited in the formula.

11. The process for producing according to claim 9, wherein a c/d ratio of the perfluoropolyoxyalkylene peroxide compound is 5.0 or less.

12. The process for producing according to claim 1, wherein a PO value of the perfluoropolyoxyalkylene peroxide compound is 8.6 or less.

13. The process for producing according to claim 1, wherein a number average molecular weight of the perfluoropolyoxyalkylene peroxide compound is 5,000 or more.

14. The process for producing according to claim 1, wherein a channel width of the microreactor is 10 mm or less.

15. The process for producing according to claim 1, wherein a channel width of the microreactor is 5.0 mm or less.

* * * * *